United States Patent
Kristiansen

(10) Patent No.: US 7,266,996 B2
(45) Date of Patent: Sep. 11, 2007

(54) PERCOLATION TESTING APPARATUS AND METHOD

(75) Inventor: Robert Kristiansen, 141 Black Rd., Shokan, NY (US) 12481

(73) Assignee: Robert Kristiansen, Shokan, NY (US)

( * ) Notice: Subject to any disclaimer, the term of this patent is extended or adjusted under 35 U.S.C. 154(b) by 101 days.

(21) Appl. No.: 11/160,187

(22) Filed: Jun. 13, 2005

(65) Prior Publication Data

US 2006/0277980 A1 Dec. 14, 2006

(51) Int. Cl.
*G01N 15/08* (2006.01)
(52) U.S. Cl. .......................................... 73/73
(58) Field of Classification Search ............. 73/38, 73/73, 152.06, 319, 321, 314
See application file for complete search history.

(56) References Cited

U.S. PATENT DOCUMENTS

| | | | | |
|---|---|---|---|---|
| 3,892,126 A | * | 7/1975 | Curtin | 73/38 |
| 3,945,247 A | * | 3/1976 | Anderson | 73/73 |
| 3,954,612 A | * | 5/1976 | Wilkerson | 210/86 |
| 4,182,157 A | * | 1/1980 | Fink | 73/38 |
| 4,341,110 A | | 7/1982 | Block | |
| 4,561,290 A | * | 12/1985 | Jewell | 73/38 |
| 4,827,762 A | * | 5/1989 | Hasselmann | 73/49.2 |
| 4,829,817 A | * | 5/1989 | Kozlowski | 73/152.41 |
| 4,984,447 A | * | 1/1991 | Phillips | 73/38 |
| 5,483,831 A | * | 1/1996 | Steiner | 73/313 |
| 5,524,487 A | * | 6/1996 | Liu | 73/313 |
| 5,950,487 A | * | 9/1999 | Maresca et al. | 73/293 |
| 6,938,461 B1 | * | 9/2005 | Johnson | 73/38 |

* cited by examiner

*Primary Examiner*—Hezron Williams
*Assistant Examiner*—John Fitzgerald

(57) ABSTRACT

An apparatus and method which accurately quantifies the percolation rate of soils, or other materials. This invention unlike prior arts measures the time elapsed for water to drop in a percolation test hole between two fixed points. The elevation of the water is electronically detected which provides signaling to control circuitry that starts and stops an electronic timer and other peripheral circuitry to automate testing. The information gathered is typically used for the design of wastewater and storm water disposal systems.

3 Claims, 1 Drawing Sheet

PERCOLATION TESTING APPARATUS AND METHOD

BACKGROUND OF THE INVENTION

Figure 1:
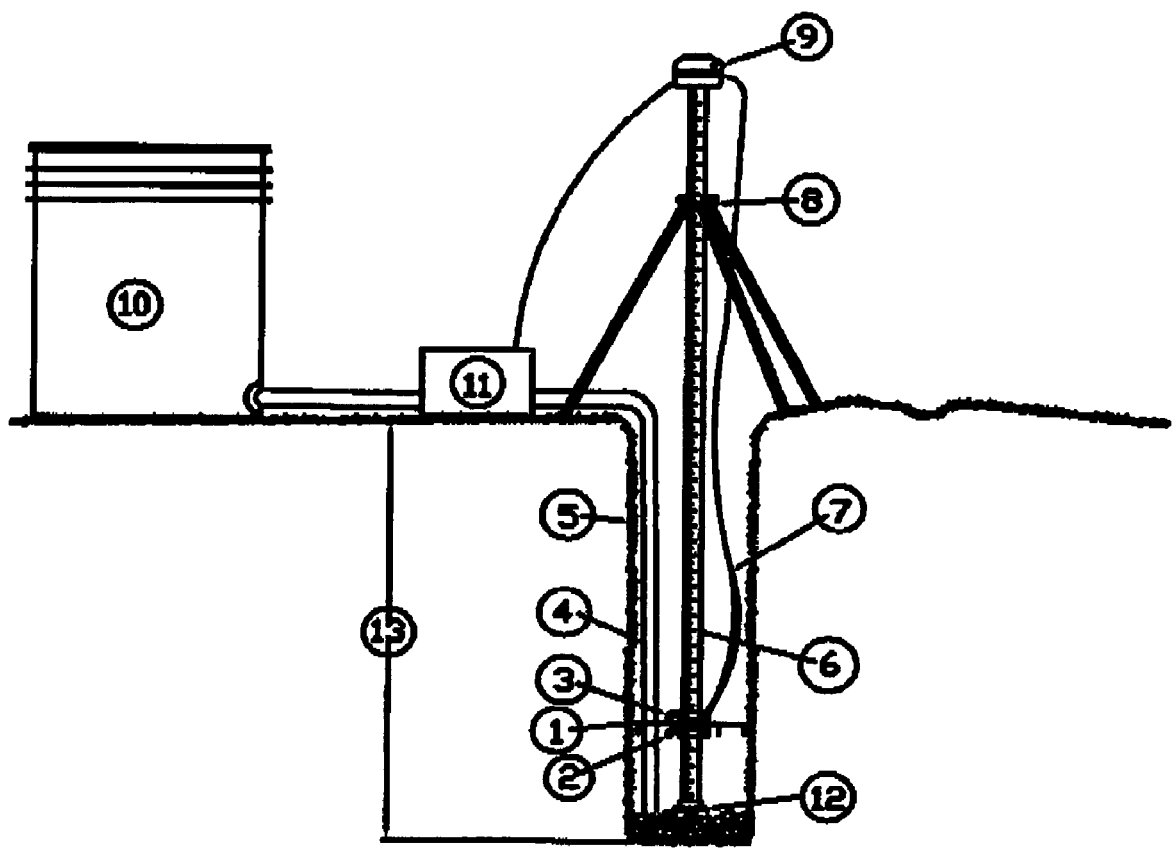

Percolation testing has long been a method to identify the absorption and treatment properties of soil or other media. In the conventional or current method a test hole is dug to the depth of the proposed disposal field system and a couple inches of gravel is placed in the bottom. The hole is then filled with water to presoak the soils. After the hole is empty, water is poured into the test hole to a specified elevation typically marked on a stick with a nail or a line. A second mark is placed on the same stick a measured distance below the first. As the water passes the first mark a start time is recorded and the waters decent is constantly monitored until the second line is reached by the top of the water. The ending time is recorded when the water level reaches the second (or lower) mark. This timing of the water dropping between the upper and lower mark is repeated until two recorded runs are the same showing a "stabilized" percolation rate. This stabilized rate is used in conjunction with known standards to size the disposal or absorption system. As identified above, one problem that exists with the current testing method is the requirement to constantly monitor the drop of water in the test hole to properly determine the end time. Inaccuracies are commonly created when reading the start and stop locations in a test hole since visibility is very limited by the test hole sides. Finally, since a stabilized percolation rate is the design parameter sought, the multiple tests required for a single test hole consumes many man hours.

PRIOR ART

Patent #4,341,110 makes reference to other prior arts: U.S. Pat. Nos. 3,926,143, 3,945,247, 4,099,406 and 4,182,157 all of which require continual operator supervision. In Patent No. 4,341;110 the inventor utilizes a recording medium which tracks the decent rate of the percolating water as it is absorbed in the test hole. The art defined in Patent #4,341,110 while it makes mention of a timer, records distance instead of time. This testing method implemented is inaccurate since the art records distance by marking a medium at fixed time intervals. The marks made have to then be correlated with the elevation in the hole where the time intervals occurred which requires extensive set up and measuring.

The present invention overcomes this deficiency and numerous other disadvantages by enabling the user to set the specific start and stop positions within the test hole. Measuring time rather than distance is the more accepted method of percolation testing since variations from hydraulic pressure and soil changes along the test hole depth are eliminated.

DETAILED DESCRIPTION

The present invention enables anyone with minimal skill to conduct accurate soils testing consistent with locally accepted methods. This testing apparatus has two detectors which are vertically adjustable on a scaled vertical member. The said vertical member rests on top of the gravel placed at the bottom of the test hole. Above the test hole, the main vertical member is horizontally supported by a vertically adjustable tripod assembly. Each detector is connected to the control circuit which as shown in the drawing may be mounted on the main vertical support or set near the test hole. The control circuit provides signaling to the timer to start, stop and store times. Additionally, the control circuit drives the control valve which provides source water as needed during repetitive test runs. Finally, the control circuit provides hole filled notification and test complete alarms (audible and visual). The timer circuit can be integrated with the control circuit or a stand-alone timer can be connected to the control circuit. The timer circuit will display the test times with a standard LCD or similar display. In addition, the timer circuit will provide user control of reset and data retrieval functions.

The general operation of this apparatus is as follows: The two detectors are set to the desired test elevations which are specified typically by local governing agencies or accepted standards. These set points are defined to standardize testing and provide prescriptive methods for disposal system designs. For example the state or local health department may require a 26 inch deep test hole and the testing of water absorption to be conducted between 6 inches from the bottom to 5 inches from the bottom, the detectors will be adjusted to these points. Should a test require different spacing of the detectors such as 4 inches to get a better averaging for storm water disposal, the detectors are independent of each other and can be adjusted to any elevation on the main vertical member. As the water drops, the timer start is initiated with the upper detector signaling the control circuit and continues until the lower detector automatically stops the timer. The user then records the displayed time (percolation time) and resets the timer. The test hole then can be refilled with water and a second test can be conducted. By having this said apparatus in service, the user is capable of running several test holes simultaneously. When a percolation test has been completed the time stays on the timer display until the user resets the timer. With this mode of operation each timed test-run requires the user to refill the hole with a water to the proper level. An alternate mode of this device shall be where multiple unmanned test times are desired. This alternate mode shall utilize a water source fed by gravity such as an elevated bucket or a pressurized source in conjunction with a electronically controlled valve.

Operating the Unit in Alternate Mode:

The device is installed in the test hole and the necessary water source feed is routed through the electronic controlled valve and into the said test hole.

1. The timer is initialized and the control valve is opened by the electronic controller.
2. Water fills the test hole until the upper detector signals the proper level has been reached.
3. This upper detector signaling causes the said electronic valve to close stopping said source water from flowing into the test hole. The water level in the test hole now shall start to drop.
4. The upper detector provides a secondary signal indicating the water has dropped to initiate the first timed event. Time elapses (based on soil infiltration rate) and the water drops to the lower detector set point, which causes the lower detector to signal the control circuit.
5. The control circuit provides a signal to stop the timer for the current event. In addition, the control circuit provides a signal to store the event time and restart the sequence described above starting with step 2.

The user shall have the option to set the number of cycles electronically or through limiting the source water volume. The following novelties exist in this invention that did not exist in any prior art.

1. The user can set up multiple test holes and run simultaneous tests.
2. Each timed event is controlled electronically which enables superior accuracy and repeatability.
3. Since this apparatus partially automates this testing in both modes of operation, the user will save many man hours. For example; on sites where percolation rates are slow the user may opt to set up this apparatus so that tests are conducted unmanned overnight.

A version of the apparatus assembly depicted in FIG. 1 is shown placed in a rests on a apparatus foot (12) that is steadied by the bottom of the test hole. The main member (6) is steadied by the tripod support assembly (8) and continues upward to provide support for the control module/display user interface (9). Control module (9) connects to lower detector (2) and upper detector (3) via detector control leads (7). A water source (10) which could be a container or pressurized source is coupled to a control valve (11) which starts and stops water flow through water supply line (4) into test hole (1) Control module (9) is connected to control valve (11) to sequence the refilling of the test hole (1) between successive percolation tests. Percolation test hole depth (13) is typically controlled by local standards or professional practice and site conditions.

What is claimed is:

1. An apparatus for testing the water absorption or percolation of soil where said apparatus is comprised of a scaled main vertical support; two electronic detectors mounted adjustably on said vertical support; an electronic control module to receive signals of said detectors and provide start and stop signals to an electronic timer circuit; a tripod support assembly which adjusts vertically and locks on said main vertical support to maintain said apparatus in a vertical position.

2. An apparatus as defined in claim 1 wherein said control module additionally controls an electronic valve to fill and refill a test hole with water to perform multiple percolation tests, a secondary signal provided by said control module to said timer circuit which shall cause the storage of the previous test, in units of time, in a memory; and clear the timer and initiate the timing of a new percolation test.

3. An apparatus as defined in claim 2 which can repeat a percolation test and store the elapsed time of the test in memory for a predetermined number of times or can be limited by the quantity of source water to be provided.

* * * * *